United States Patent [19]

McAvinn et al.

[11] 4,244,369
[45] Jan. 13, 1981

[54] SURGICAL SPONGE WITH VISUALLY DETECTABLE ELEMENT

[75] Inventors: James D. McAvinn, Chicago; Herbert G. Canty, Ingleside, both of Ill.

[73] Assignee: The Kendall Company, Boston, Mass.

[21] Appl. No.: 15,074

[22] Filed: Feb. 26, 1979

Related U.S. Application Data

[63] Continuation-in-part of Ser. No. 760,056, Jan. 17, 1977, abandoned.

[51] Int. Cl.³ .............................................. A61F 13/00
[52] U.S. Cl. .................................................... 128/296
[58] Field of Search ................................ 128/155–156, 128/290, 296; 428/379, 380, 383, 377; 57/223, 234, 241–242, 258

[56] References Cited

U.S. PATENT DOCUMENTS

| | | | |
|---|---|---|---|
| 2,698,270 | 12/1954 | Mesek | 128/296 |
| 3,133,538 | 5/1964 | Pratt et al. | 128/296 |
| 3,464,415 | 9/1969 | Brownlee | 128/296 |
| 3,608,298 | 9/1971 | Schoots | 428/383 |
| 3,698,393 | 10/1972 | Stone | 128/296 |
| 3,736,935 | 6/1973 | Reimels | 128/296 |
| 3,756,241 | 9/1973 | Patience | 128/296 |
| 3,941,132 | 3/1976 | Lenaghan | 128/296 |

FOREIGN PATENT DOCUMENTS

| | | | |
|---|---|---|---|
| 814668 | 6/1969 | Canada | 428/379 |
| 948387 | 6/1974 | Canada | 128/296 |
| 736685 | 9/1955 | United Kingdom | 128/296 |
| 805082 | 11/1958 | United Kingdom | 128/296 |
| 922692 | 4/1963 | United Kingdom | 428/379 |
| 961391 | 6/1964 | United Kingdom | 428/379 |
| 1274061 | 5/1972 | United Kingdom . | |

*Primary Examiner*—Robert W. Michell
*Assistant Examiner*—C. F. Rosenbaum
*Attorney, Agent, or Firm*—Powell L. Sprunger

[57] ABSTRACT

A surgical sponge comprising, a sheet of an absorbent material, and an elongated visually detectable element at least partially located on an outer surface of the sheet, with the element being non-wettable and of a color which contrasts with the color of blood to significantly increase the visibility of the sponge in a patient's body when saturated by body fluids.

2 Claims, 8 Drawing Figures

SURGICAL SPONGE WITH VISUALLY DETECTABLE ELEMENT

BACKGROUND OF THE INVENTION

This application is a continuation-in-part of application Ser. No. 760,056, filed Jan. 17, 1977, now abandoned.

The present invention relates to absorbent articles, and more particularly to surgical sponges.

Surgical sponges are commonly used during surgical procedures to absorb body fluids of the patient both inside the incision and around the site of surgery. Sponges of this nature are usually made of an open-meshed absorbent fabric, such as woven cotton.

It is important, of course, that all of such sponges be removed from the patient's body after surgery is complete and before the incision has been closed. Accordingly, it is a standard procedure for the surgical team to carefully count the sponges to reduce the possibility that a sponge may be left in the patient.

In spite of such safety measures, sponges have been occasionally lost, particularly when an unexpected emergency disrupted the normal operative routine such as counting, which is subject to human error. When saturated by body fluids, such as blood, the sponges become significantly reduced in size and assume a color the same as body tissue, thus making visual detection of the sponges extremely difficult. As a result, it has been required to provide the sponges with a flexible insert which is opaque to X-rays. In case of a disputed or non-tallying sponge count is the operating room, or in case of unexpected or unexplainable post-operative discomfort on the part of the patient, a portable X-ray unit is brought to the patient and an X-ray exposure should reveal the presence or absence of a lost sponge. A negative plate should be reassurance to the surgeon that he and his operative team have not left a sponge in the patient. Nevertheless, it is desirable that the patient be provided additional assurance a sponge does not remain in his body, and that the number of instances an X-ray is necessary be minimized, whether or not additional surgery would ultimately be required to remove a lost sponge.

SUMMARY OF THE INVENTION

A principal feature of the present invention is the provision of a surgical sponge of simplified construction which prevents mishaps in reclaiming sponges from a patient's body.

The sponge of the present invention comprises, a sheet of an absorbent material, and an elongated visually detectable element as least partially located on an outer surface of the sheet. The element is constructed from a highly reflective material having a color which contrasts with the color of blood, a fluorescent material, a phosphorescent material, or an iridescent material, with the element including an outer non-wettable transparent surface having a contact angle greater than 90 degrees in the presence of blood.

A feature of the present invention is that the element substantially increases the visibility of the sponge in the patient's body.

Another feature of the present invention is that the element permits visual detection of the sponge even when the sheet is saturated with body fluids.

Thus, a feature of the present invention is that the element minimizes the possibility that the sponge may be left in a patient's body during an operation.

Further features will become more fully apparent in the following description of the embodiments of this invention and from the appended claims.

DESCRIPTION OF THE PREFERRED EMBODIMENTS

Figure 1:
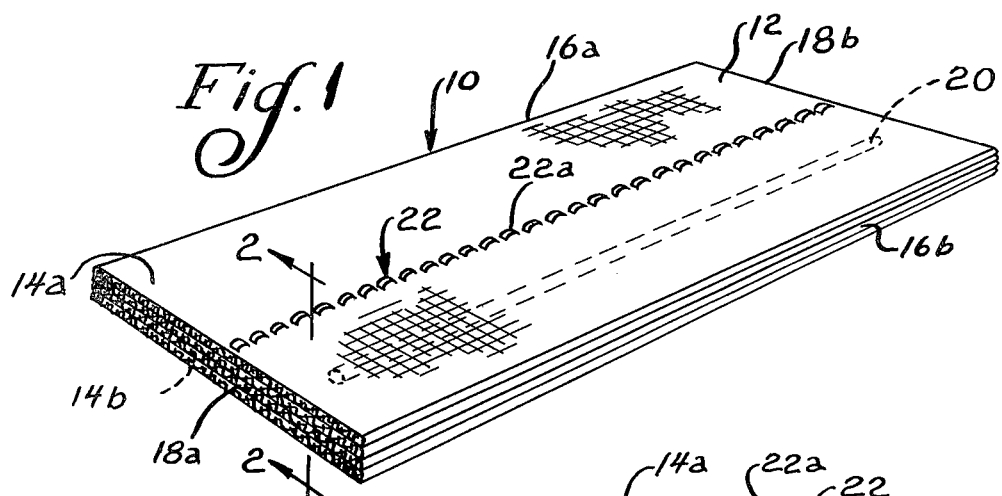
FIG. 1 is a perspective view of a surgical sponge of the present invention having a visually detectable element.
Figure 2:
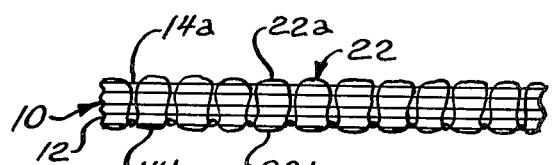
FIG. 2 is a fragmentary sectional view taken substantially as indicated along the line 2—2 of FIG. 1.

Referring now to FIGS. 1 and 2, there is shown a surgical sponge generally designated 10 having a sheet 12 of an absorbent material, e.g., a low-count gauze-like or open-mesh fabric, such as woven cotton, or a nonwoven material. The sheet 12 has a plurality of folds defining a multiple ply of the sponge 10, with the folded sponge having a pair of opposed outer surfaces 14a and 14b, a pair of side edges 16a and 16b, and a pair of end edges 18a and 18b connecting the side edges 16a and b. The sponge 10 may have an elongated radiopaque filament 20 located between plies of the sheet 12 to prevent dislodgment of the filament 20 from the sponge 10 during use in surgery. The filament 20 may be made of a thermoplastic polymeric material containing a radiopaque material, such as barium sulfate, such that it may be detected on an X-ray photograph.

Figure 3:
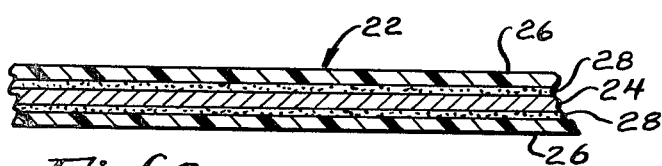
FIG. 3 is a fragmentary sectional view on an enlarged scale of an element suitable for the sponge of FIG. 1.

The sponge 10 also has an elongated visually detectable element 22 secured at least partially on an outer surface of the absorbent sheet or fabric 12. In a preferred form, the element 22 is highly reflective and has a color which contrasts with the color of blood and is non-wetting. A suitable material for the element 22 is a thread sold by Metlon Corporation, Providence, R.I. With reference to FIG. 3, such a thread is substantially non-radiopaque to X-rays, and has a central layer 24 of metallic material, such as aluminum foil or stainless steel, a pair of outer layers 26 of transparent plastic material, such as polypropylene or Mylar, a trademark of E. I. du Pont de Nemours, on opposed sides of the central layer 24, and layers 28 of a thermoplastic adhesive bonding the outer transparent layers 26 to opposed surfaces of the central metallic layer 24. If the adhesive 28 in the laminate is transparent, then the element 22 assumes the color of the metallic layer 24, e.g., a highly reflective silver or gold color which is suitable for the element 22 on the sponge 10. Alternatively, the adhesive 28 may be provided with a dye in order to color the thread in a desired manner, such as a gold color, while providing the thread with a highly reflective colored surface due to the metallic base of central layer 24 which underlies the colored adhesive layers 28. In use, the outer plastic layers 26 protect the dye in the adhesive and prevent the element from becoming colored by body fluids, such as blood. The described element is substantially non-toxic and non-abrasive to body tissues.

As discussed below, the transparent layers 26 of the element 22 cause the element to be non-wettable in the presence of blood. When a liquid, such as blood, contacts a flat surface of a solid material, the liquid will either bead up on the solid material or will spread out to form a film on the material surface. In the former beading case, the liquid is said not to wet the material surface, and the beads of liquid easily roll off the material surface when it is tilted. In the latter spreading case, the liquid is said to wet the material surface.

For a given solid surface, the degree of wettability relative to a specified liquid is determined experimentally by the contact angle $\theta$ formed by the liquid on the surface. If the contact angle is greater than 90 degrees, the specified liquid is said to not wet the solid, while if the contact angle is less than 90 degrees, the liquid is said to wet the solid. It is known that the different contact angles formed by various liuids on a given solid are dependent upon the respective surface tensions of the liquids. It has been found that if different liquids of increasing surface tension are successively placed upon a given solid material, the corresponding values of $\cos \theta$ decrease in a linear fashion, where $\theta$ is the contact angle between the different liquids and the solid, i.e., the contact angle $\theta$ increases for liquids of increasing surface tension, and the liquids wet the solid less for the increasing contact angle. If, for a given solid material, the above-described values of $\cos \theta$ for the different testing liquids are plotted against the corresponding surface tensions of the liquids, the points define a line on the graph, termed a Zisman plot. If the line is extended to cut the axis associated with the surface tensions, the point defined by the intersecting line and surface tension axis corresponds to the surface tension, termed the critical surface tension, where $\cos \theta = 0$ ($\theta = 90$ degrees). For the given solid material, a liuid having a surface tension less than the critical surface tension associated with the solid material will wet the solid, while a liquid having a surface tension greater than the critical surface tension of the solid material will not wet the solid. Thus, the critical surface tension of the solid defines a demarcation between wetting and non-wetting liquids, such that the solid will be wet only by those liquids having a surface tension less than the critical surface tension of the solid. The following table sets forth data obtained from various sources for the approximate surface tension of specified liquids, the approximate contact angle of specified solids in the presence of water, and the approximate critical surface tension of specified solids.

| Liquid | Surface Tension (erg./cm.$^2$) | Solid | Contact Angle with Water (degrees) | Critical Surface Tension (dynes/cm.) |
|---|---|---|---|---|
| | | polytetrafluoroethylene (Teflon) | 112 | 18.5 |
| | | polypropylene | 108 | 30.0 |
| | | polyethylene | 103 | 31.0 |
| | | polyethylene | | |

-continued

| Liquid | Surface Tension (erg./cm.$^2$) | Solid | Contact Angle with Water (degrees) | Critical Surface Tension (dynes/cm.) |
|---|---|---|---|---|
| | | terephthalate (Mylar) | | 43.0 |
| | | polyvinyl chloride | | 39.0 |
| | | gold | 66 | |
| | | platinum | 40 | |
| | | silver | 90 | |
| water | 72 | | | |
| blood | 60 | | | |

Since the surface tension of blood is less than the surface tension of water, blood wets a given solid more than water, and if the solid is wetted by water it is wetted by blood. Accordingly, since the contact angles of gold and platinum in the presence of water are less than 90 degrees, gold and platinum are wetted by water and thus by blood. Also, since the contact angle of silver in the presence of water is approximately equal to 90 degrees, and since the surface tension of blood is less than the surface tension of water, the contact angle of silver in the presence of blood is less than 90 degrees, and thus blood wets silver. However, since the surface tensions of water and blood are both greater than the critical surface tensions of the listed polymers (polytetrafluoroethylene, polypropylene, polyethylene, polyethylene terephthalate, and polyvinyl chloride), the polymers are not wetted by water or blood. Thus, according to the present invention, the transparent layers 26 of the element 22 are not wetted in the presence of blood, in contrast to the noble metals, in order to prevent spreading of blood along the transparent surface of the element and enhance visibility of the element in the presence of body liquids.

In a preferred form, the element 22 is relatively flexible and thin in order that it may be sewn into the fabric or gauze sheet 12 by a sewing machine as the thread in a sewing pattern. With reference to FIG. 2, in a lock stitch threads of the element may be sewn through the machine needle and from the bobbin, such that the sewn sponge 10 has a pair of visually detectable elements 22a and 22b on the opposed surfaces 14a and b of the sponge. Alternatively, a visually detectable thread may be utilized in a chain stitch to provide the sponge with portions of the thread on the opposed surfaces of the sponge. Of course, the element 22 may be attached to the outer surface of the sponge by any suitable means, such as lines of stitching, but in a preferred form the element may be conveniently sewn into the fabric in a simplified manner during construction of the sponge and preventing dislodgement of the element during use of the sponge.

In accordance with the present invention, the sponge 10 has a highly reflective non-wettable element 22 at least partially on an outer surface of the sponge, such that the reflective element is readily visible even when the sheet 12 of absorbent material has been saturated by body fluids, such as blood. Accordingly, the reflective element 22 permits visibility of the sponge in the patient's body in order to minimize the possibility that the sponge may become lost during surgery and to reduce the number of instances in which an X-ray unit must be utilized to locate a lost sponge. In this regard, it is noted that the radiopaque elements commonly used in surgical sponges are normally located within plies of the sponge material, and are not normally visible on the outside of the sponge. Further, even if positioned on the outer surface of the sponge, such radiopaque elements do not have a sufficiently reflective surface to enhance visual recognition of the sponge.

Figure 6:
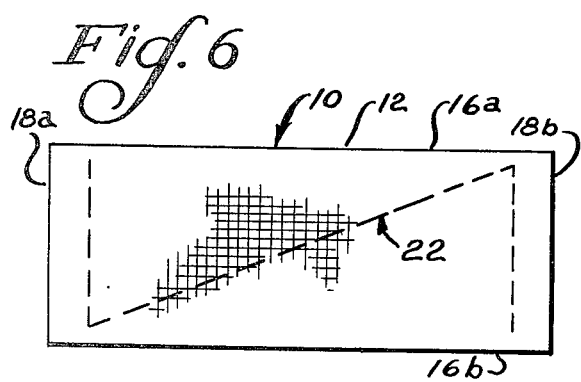
FIGS. 6 and 7 are plan views of absorbent sponges having differing patterns formed by visually detectable elements.
Figure 7:
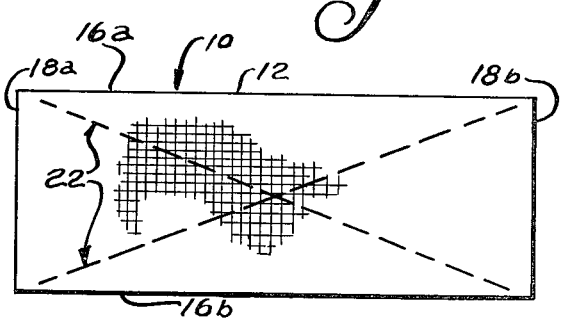

In a preferred form, the reflective element 22 extends throughout a substantial area of the folded sponge 10. As shown in FIG. 1, the element 22 may extend the length of the folded sponge between the end edges 18a and b. Other suitable configurations of the element 22 comprise a plurality of spaced lines, a pattern generally in the shape of a Z, as shown in FIG. 6, or a pattern in the shape of an X, as shown in FIG. 7, such that the reflective element 22 extends substantially the width and length of the sponge between its side and end edges in order to insure that the reflective element is readily visible on the outer surface of the sponge.

In an alternative form, the element 22 may be made from a light emitting material, such as a flourescent or phosphorescent material, or from an irridescent material, with the element having an outer transparent nonwetting surface, as previously described. As known, a flourescent material, such as a film sold by Appleton Papers, Appleton, Wisconsin, emits electromagnetic radiation as a result of energy flow, such as light, into the emitting body so long as the excitation continues, while a phosphorescent material is luminescent after the source of excitation ceases. An irridescent material, such as a film sold by The Mearl Corporation, Peekskill, N.Y., displays a rainbow color effect as a result of interference in a thin film or diffraction of light reflected from a ribbed surface. In either event, an element 22 made of such materials and the above-described transparent surface layers significantly increases the visibility of the sponge when wetted with body fluids during use.

Figure 4:
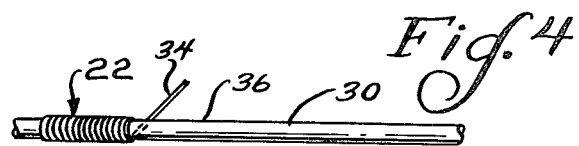
FIG. 4 is a fragmentary elevational view of a partially formed element for the sponge of the present invention.
Figure 5:
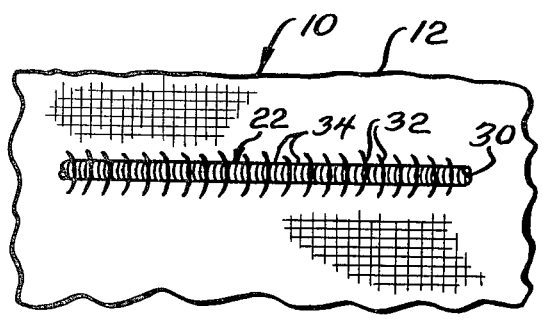
FIG. 5 is a fragmentary plan view of a surgical sponge having an element as constructed in accordance with the element of FIG. 4.

Another embodiment of the present invention is illustrated in FIGS. 4 and 5, in which like reference numerals designate like parts. In this embodiment, the visually detectable element 22 comprises an elongated ribbon 30 of radiopaque material, such as a thermoplastic material impregnated with barium sulfate, which has a formed highly reflective outer layer, or other visually detectable outer layer, as previously described. The outer surface may be formed by winding a visually detectable thread or yarn 34, with the desired detectable surface characteristics, around and covering an outer surface 36 of the radiopaque ribbon 30. The detectable yarn 34 may be of the types previously described, and the formed visually detectable element 22 may be secured on the outer surface of the sheet 12 by suitable means, such as by stitching 32 shown in FIG. 5. Thus, the element 22 has an inner radiopaque ribbon 30 which may be utilized, if necessary, for detection of the sponge by an X-ray unit. Additionally, the element 22 has a non-wettable visually detectable outer surface defined by the yarn 34 to significantly enhance visual detection of the sponge when located in the patient's body and saturated with body fluids, thus minimizing the possibility that the sponge may become lost in the body and that an X-ray exposure of the body may be required. The sponge of FIGS. 4 and 5 may have a fabric of the type discussed in connection with FIGS. 1-3.

Figure 8:
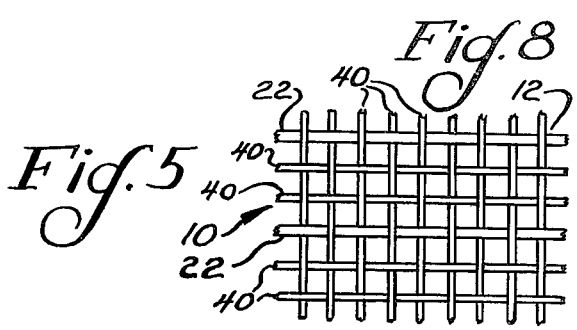
FIG. 8 is a fragmentary plan view of a fabric in which the element is formed as an integral part of the fabric structure.

Another embodiment of the present invention is illustrated in FIG. 8, in which like reference numerals designate like parts. In this embodiment, the previously discussed visually detectable element 22 may be woven into the fabric or sheet 12 as a yarn, while the remaining yarns 40, such as cotton, provide absorbency for the sponge 10. Alternatively, the described element 22 may be utilized as a yarn in a knitted fabric.

The foregoing detailed description is given for clearness of understanding only, and no unnecessary limitations should be understood therefrom, as modifications will be obvious to those skilled in the art.

We claim:

1. A surgical sponge, comprising:
   a sheet of an absorbent material comprising a multiple ply absorbent gauze; and
   an elongated visually detectable element having a portion at least partially located on an outer surface of said sheet, said element being substantially non-radiopaque to X-rays and comprising an inner layer of a highly reflective material, and an outer layer at least substantially covering the inner layer, said outer layer comprising (a) transparent material means for defining a nonwettable outer surface of the element, said outer surface having a contact angle greater than 90 degrees in the presence of blood whereby in the presence of blood, at least portions of said element are not occluded by blood and thus remain highly visible, said non-wettable element having a color which contrasts with the color of blood to further significantly increase the visibility of the sponge in a patient's body when said sponge is saturated by body fluids, said outer portion extending a substantial distance along the outer surface of the sheet and being permanently affixed to the sheet throughout its length.

2. The sponge of claim 1 including a separate radiopaque element located on said sheet.

3. The sponge of claim 1 wherein said sheet comprises a multiple-ply absorbent gauze.

4. The sponge of claim 1 wherein said element includes a central layer, in which said outer layer comprises a pair of transparent films on opposed sides of the central layer, and in which said inner layer comprises a highly reflective adhesive bonding the films on opposed surfaces of the central layer.

5. The sponge of claim 1 wherein said inner layer comprises, a central layer of a highly reflective metallic material, in which the outer layer comprises a pair of outer films of a transparent material on opposed sides of said central layer, and in which the element includes a transparent adhesive bonding said outer films on opposed surfaces of the central layer.

6. The sponge of claim 5 wherein said adhesive contains a coloring material.

7. The sponge of claim 1 wherein said element is relatively narrow and comprises a thread in a stitching pattern sewn onto said sheet.

8. The sponge of claim 1 wherein said element defines a pattern on the surface of said sheet extending substantially throughout the width and length of the sponge.

9. The sponge of claim 1 wherein said element is secured on an outer surface of said sheet.

10. The sponge of claim 1 wherein said sheet comprises a fabric having a plurality of absorbent yarns and said element is an integral part of the fabric structure.

11. The sponge of claim 10 wherein said element is woven into said fabric with said absorbent yarns.

12. The sponge of claim 1, further comprising an elongate radiopaque ribbon, said elongated visually detectable element being wound about said elongate radiopaque ribbon.

13. A surgical sponge, comprising:

a sheet of an absorbent material comprising a multiple ply absorbent gauze; and an elongated visually detectable element having a portion at least partially located on an outer surface of said sheet, said element being substantially non-radiopaque to X-rays and comprising an inner layer of a fluorescent material, and an outer layer at least substantially covering the inner layer, said outer layer comprising transparent material means for defining a non-wettable outer surface of the element, said outer surface having a contact angle greater than 90 degrees in the presence of blood whereby in the presence of blood, at least portions of said element are not occluded by blood and thus remain highly visible, said fluorescent material inner layer contrasting with the color of blood to further significantly increase the visibility of the sponge in a patient's body when said sponge is saturated by body fluids, said outer portion extending a substantial distance along the outer surface of the sheet and being permanently affixed to the sheet throughout its length.

14. The sponge of claim 13, further comprising an elongated ribbon of radiopaque material, and in which an elongated yarn of said fluorescent material is wound about an outer surface of said ribbon.

15. The sponge of claim 13, further comprising a separate radiopaque element located on said sheet.

16. A surgical sponge, comprising:
a sheet of an absorbent material comprising a multiple ply absorbent gauze; and
an elongated visually detectable element having a portion at least partially located on an outer surface of said sheet, said element being substantially non-radiopaque to X-rays and comprising an inner layer of phosphorescent material, and an outer layer at least substantially covering the inner layer, said outer layer comprising transparent material means for defining a non-wettable outer surface of the element, said outer surface having a contact angle greater than 90 degrees in the presence of blood whereby in the presence of blood, at least portions of said elements are not occluded by blood and thus remain highly visible, said phosphorescent material inner layer contrasting with the color of blood to further significantly increase the visibility of the sponge in a patient's body when said sponge is saturated by body fluids, said outer portion extending a substantial distance along the outer surface of the sheet and being permanently affixed to the sheet throughout its length.

17. The sponge of claim 16, further comprising an elongated ribbon of radiopaque material, and in which an elongated yarn of said phosphorescent material is wound about an outer surface of said ribbon.

18. The sponge of claim 16, further comprising a separate radiopaque element located on said sheet.

19. A surgical sponge, comprising:
a sheet of an absorbent material comprising a multiple ply absorbent gauze; and
an elongated visually detectable element having a portion at least partially located on an outer surface of said sheet, said element being substantially non-radiopaque to X-rays and comprising an inner layer of iridescent material, and an outer layer at least substantially covering the inner layer, said outer layer comprising transparent material means for defining a non-wettable outer surface of the element, said outer surface having a contact angle greater than 90 degrees in the presence of blood whereby in the presence of blood, at least portions of said element are not occluded by blood and thus remain highly visible, said iridescent material inner layer contrasting with the color of blood to further significantly increase the visibility of the sponge in a patient's body when said sponge is saturated by body fluids, said outer portion extending a substantial distance along the outer surface of the sheet and being permanently affixed to the sheet throughout its length.

20. The sponge of claim 19, further comprising an elongted ribbon of radiopaque material, and in which an elongated yarn of said iridescent material is wound about an outer surface of said ribbon.

21. The sponge of claim 19, further comprising a separate radiopaque element located on said sheet.

22. A surgical sponge, comprising:
a sheet of an absorbent, nonwoven material; and
an elongated visually detectable element having a portion at least partially located on an outer surface of said sheet, said element being substantially non-radiopaque to X-rays and comprising an inner layer of a highly reflective material, and an outer layer at least substantially covering the inner layer, said outer layer comprising transparent material means for defining a non-wettable outer surface of the element, said outer surface having a contact angle greater than 90 degrees in the presence of blood whereby in the presence of blood, at least portions of said element are not occluded by blood and thus remain highly visible, said non-wettable element having a color which contrasts with the color of blood to further significantly increase the visibility of the sponge in a patient's body when said sponge is saturated by body fluids, said outer portion extending a substantial distance along the outer surface of the sheet and being permanently affixed to the sheet throughout its ength.

* * * * *